United States Patent
Maloca et al.

(10) Patent No.: US 8,025,403 B2
(45) Date of Patent: Sep. 27, 2011

(54) OPHTHALMOLOGIC APPARATUS FOR IMAGING AN EYE BY OPTICAL COHERENCE TOMOGRAPHY

(75) Inventors: Peter Maloca, Lucerne (CH); Karim Haroud, Chavannes-sur-Moudon (CH); Urban Schnell, Muenchenbuchsee (CH)

(73) Assignee: Mimo AG (CH)

( * ) Notice: Subject to any disclaimer, the term of this patent is extended or adjusted under 35 U.S.C. 154(b) by 0 days.

(21) Appl. No.: 12/527,957

(22) PCT Filed: Feb. 18, 2008

(86) PCT No.: PCT/CH2008/000067
§ 371 (c)(1),
(2), (4) Date: Aug. 20, 2009

(87) PCT Pub. No.: WO2008/101359
PCT Pub. Date: Aug. 28, 2008

(65) Prior Publication Data
US 2010/0110377 A1 May 6, 2010

(30) Foreign Application Priority Data
Feb. 23, 2007 (EP) .................... 07405056

(51) Int. Cl.
*A61B 3/14* (2006.01)
*A61B 3/10* (2006.01)
(52) U.S. Cl. .......... 351/208; 351/205; 351/206
(58) Field of Classification Search ........... 351/200–246
See application file for complete search history.

(56) References Cited

U.S. PATENT DOCUMENTS

| | | | |
|---|---|---|---|
| 4,465,348 A | 8/1984 | Lang et al. | |
| 5,255,025 A * | 10/1993 | Volk | 351/205 |
| 5,333,018 A * | 7/1994 | Heine et al. | 351/221 |
| 5,400,092 A * | 3/1995 | Schepens et al. | 351/214 |
| 5,543,866 A | 8/1996 | Van de Velde | |
| 5,841,509 A | 11/1998 | Harooni et al. | |
| 5,943,116 A | 8/1999 | Zeimer | |
| 6,293,674 B1 | 9/2001 | Huang et al. | |
| 6,325,512 B1 | 12/2001 | Wei | |
| 6,379,005 B1 | 4/2002 | Williams et al. | |
| 7,758,189 B2 * | 7/2010 | Hammer et al. | 351/206 |
| 2002/0036749 A1 | 3/2002 | Isogai | |
| 2004/0239876 A1 | 12/2004 | Levine | |
| 2006/0114411 A1 | 6/2006 | Wei et al. | |
| 2006/0187462 A1 | 8/2006 | Srinivasan et al. | |

OTHER PUBLICATIONS

Baumgartner et al. "Measurements of the Posterior Structures of the Human Eye in Vivo by Partial Coherence Interferometry using Diffractive Optics", 1997, SPIE vol. 2981, pp. 85-93.

(Continued)

Primary Examiner — Mohammed Hasan
(74) Attorney, Agent, or Firm — Ostrolenk Faber LLP

(57) ABSTRACT

An OCT appliance (optical coherence tomography appliance) comprises an OCT module and a camera for observing the fundus of an eye. By recognizing characteristic features (biometric features), the means defining the region observed by the OCT module, in particular the scanner of the OCT module, is adjusted so that a predefined region of interest is imaged by the OCT module. In preferred embodiments, the apparatus is apt to be operated by a patient himself, and the data are transferred to a clinical server so that a more frequent, hence closer observation of the eyes of the patient is possible.

29 Claims, 7 Drawing Sheets

OTHER PUBLICATIONS

International Preliminary Report on Patentability of the International Bureau dated Sep. 3, 2009 in corresponding application No. PCT/CH2008/000067, with a filing date of Feb. 18, 2008.

International Search Report dated Apr. 29, 2008, issued in corresponding international application No. PCT/CH2008/000067.

* cited by examiner

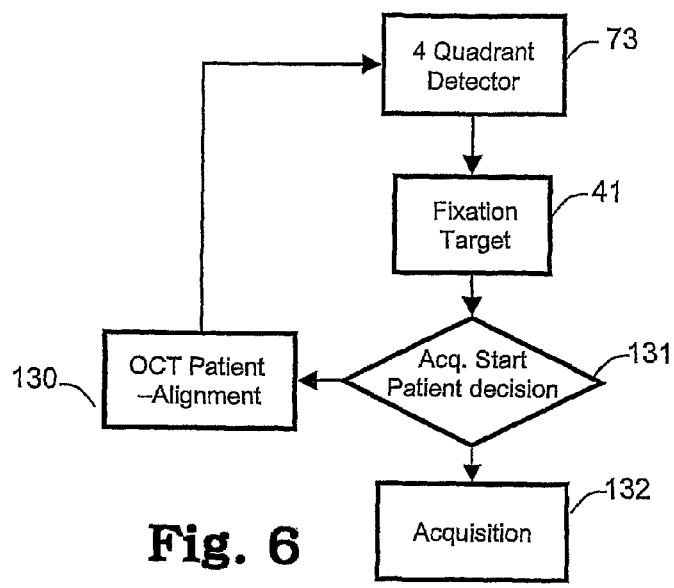
Fig. 6
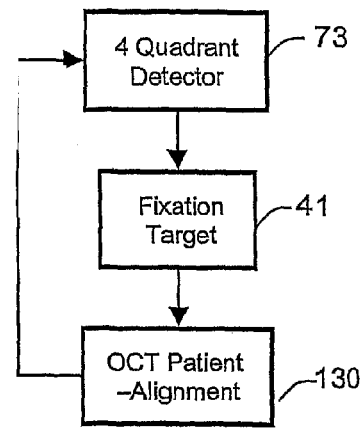
Fig. 7
Fig. 8
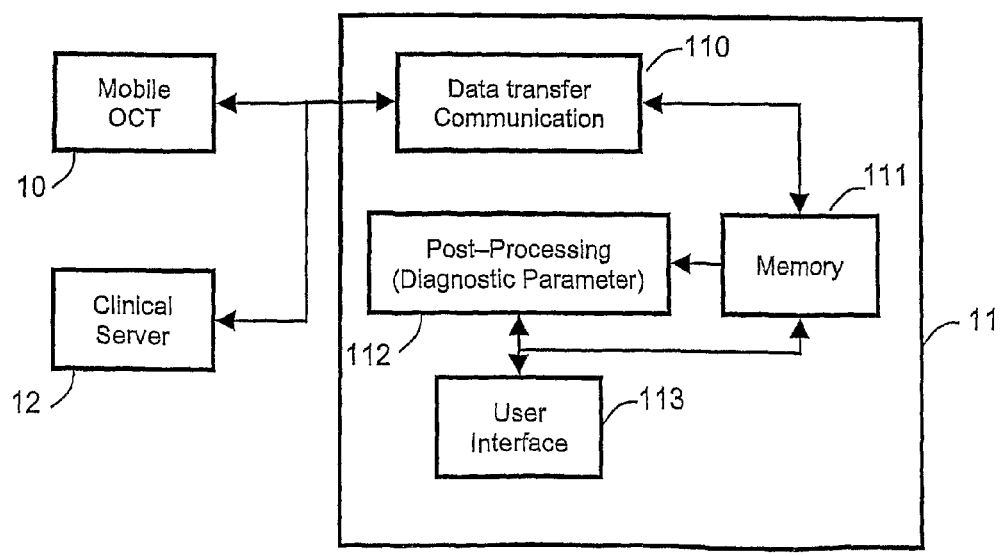

OPHTHALMOLOGIC APPARATUS FOR IMAGING AN EYE BY OPTICAL COHERENCE TOMOGRAPHY

CROSS REFERENCE TO RELATED APPLICATIONS

The present application is a 35 U.S.C. §371 National Phase conversion of PCT/CH2008/000067, filed Feb. 18, 2008, which claims benefit of European Application No. 07405056.8, filed Feb. 23, 2007, the disclosure of which is incorporated herein by reference. The PCT International Application was published in the English language.

BACKGROUND OF THE INVENTION

The present invention relates to an ophthalmologic apparatus, according to the preamble of claim 1.

Optical coherence tomography (OCT) is an established noninvasive, noncontact imaging technology which can image eye structures, and more importantly high resolution cross sectional images of the retina not only on the surface, but also up to certain depth are produced. Basics of this method is available on the internet (e.g. in the Wikipedia).

An apparatus and a method for diagnosing and monitoring eye diseases by OCT is described in U.S. Pat. No. 6,293,674. U.S. Pat. No. 6,325,512 proposes to perform relatively slow OCT scans to obtain a high signal-to-noise ratio. Eye movements during the scan are compensated by a tracking system. The tracking system uses a point photo detector and a dithering light path for scanning a certain region around a distinct point of the retina (particularly more reflective, darker etc.). Any movement out of the center of the scanned region is registered and accused to adjust mirrors in the general light path of the instrument to compensate for this movement, i.e. a movement of the eye. Obviously, this provision requires fast reacting and exact working mechanical means, hence is prone to wear and sensitive to mechanical effects (shock, vibration).

An OCT apparatus of improved vision and resolution of retinal images is presented by U.S. Pat. No. 6,379,005. The distortion of the eye is determined by observing a laser light spot on the retina using a Hartmann-Shack wavefront sensor and compensating the aberration using e.g. a deformable mirror.

This patent still contains an extensive list of patent and non-patent prior art.

All the known and described apparatuses are designed to be used by professionals and are stationary. In consequence, to begin an examination, the OCT apparatus has to be adjusted to the properties of the eye (myopic, hyperopic).

Furthermore, the professional (e.g. ophthalmologist) has to search manually a region of interest which is to be observed more closely.

OCT has proven to be a precious diagnostic tool for e.g. glaucoma, vitreo-retinal-disorders or AMD (age-related macular disease). In the latter case, OCT may not only be useful to determine the extent of the concerned region of the retina, but also to aim a laser to the correct target region for therapy.

A disadvantage of the known apparatuses is that they have to be adjusted to each patient and that the ophthalmologist or a well instructed expert has each time to search for the region of interest and to perform the corresponding adjustments manually.

Another aspect is that in many cases, the state of the eyes of a patient, and more particularly one or more distinct "regions of interest" (ROI), have to be examined regularly in order to determine as early as possible a change thereof. However, due to the fact that the patient has to visit a professional therefor, it was impossible to perform the examinations as often as desirable.

US-A-2006/0187462 discloses an automatic method of obtaining OCT images of the retina. The OCT device first performs linear survey OCT scans. Each such scan consists of two linear scans yielding each a cross-section of the retina oriented about orthogonally with respect to each other. From the position of a characteristic land mark feature in the images, a correction of the orientation of the device is calculated to center it on the land mark. Generally, due to irregularities of the eye, this procedure has to be performed more than once to achieve an exact aiming of the device. Then the actual OCT image is taken.

The survey scans are performed sufficiently rapidly that a misalignment due to eye movements is avoided.

This approach requires a particular design of the OCT unit to allow high precision and survey scans, and algorithms for rapid evaluation of the survey scans.

SUMMARY OF THE INVENTION

Hence, one object of the invention is to propose an ophthalmic apparatus with reduced adjustment demands.

Another object is to propose such an apparatus which is operable by a patient in order to allow the examination by the patient himself.

Still another object is to propose an ophthalmic apparatus wherein automatic aiming of the OCT unit is achieved by another means than an OCT survey scan.

A device is defined in claim 1 satisfying the first object. The further claims propose preferred embodiments and uses thereof.

In general, the device comprises a fundus camera for taking a picture of the fundus of the eye of a patient. Based on this image, the actual position of the eye with respect to the device can be exactly determined, and the OCT can be automatically directed to the ROI. For this purpose, characteristic feature of the retina may be used similarly to the access control systems based on eye imaging.

Preferably, the device has at least a binocular housing, more preferably is capable to measure both eyes. The binocular housing, when put before the eyes of a patient, already safeguards an almost proper position and an alignment with the axis connecting the eyes. Thereby, it is rendered easier, before all if used by the patients autonomously, to hold the device in a position within the working range of the means for adjusting the OCT based on the image taken by the fundus camera.

Another advantage of the device is attained if the patient gets its own apparatus. Then, the apparatus may be adjusted to his/her viewing capabilities (adjustment of dioptries etc.), and the interpupillary distance (IPD). Hence, it is no more necessary to calibrate the apparatus, or only a fine adjustment is still necessary.

Furthermore, the apparatus may be capable to have an external device, e.g. a thermal laser for therapeutic purposes, coupled to it, whereby again a rapid and real-time-control treatment in the region of interest (ROI) without preceding individual adjustment is possible.

BRIEF DESCRIPTION OF THE DRAWINGS

These and other advantages of the invention will be further demonstrated by means of preferred exemplary embodiments illustrated by the attached Figures.

FIG. 6 Flow diagram of pupil alignment feedback before measurement;

FIG. 7 Flow diagram of pupil alignment feedback during measurement;

FIG. 8 Block diagram of data transfer and post-processing;

DESCRIPTION OF PREFERRED EMBODIMENTS

Figure 1:
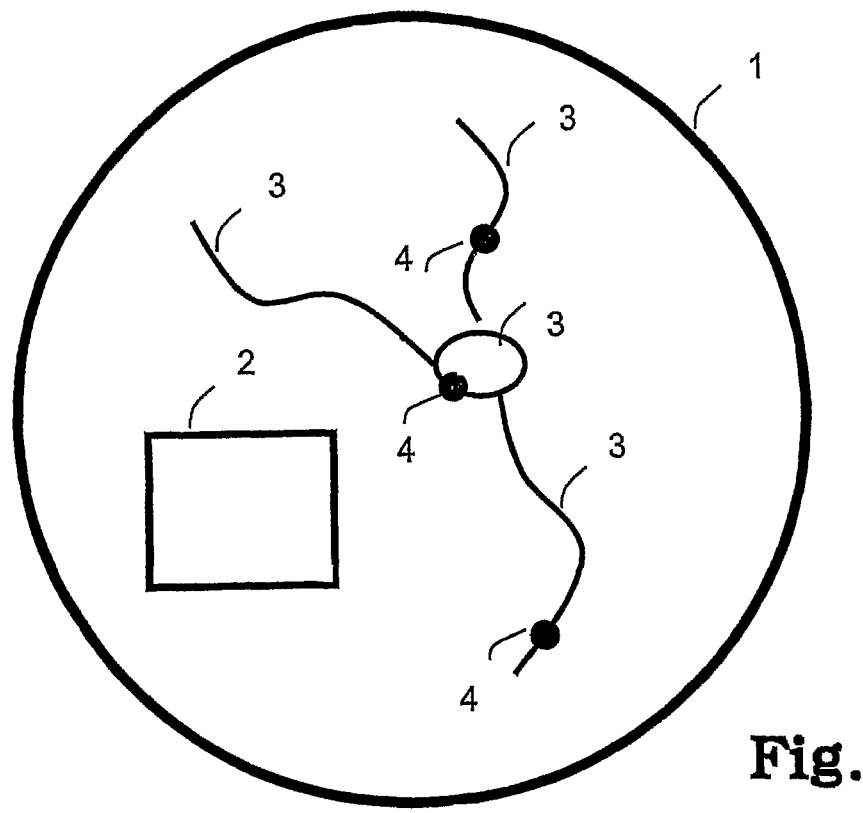
FIG. 1 A schematic image of the retina.

FIG. 1 illustrates the image taken by a fundus camera in a schematized style. The image 1 comprises details of the eye's retina. Within the biometric features 3 of the retina, markers 4 can be defined which are linked be the biometric features 3. Relative to the markers 4, the region of interest (ROI) 2 is defined. Of course, it is possible to have more than one single ROI defined, and another number of markers can be used.

Figure 2:
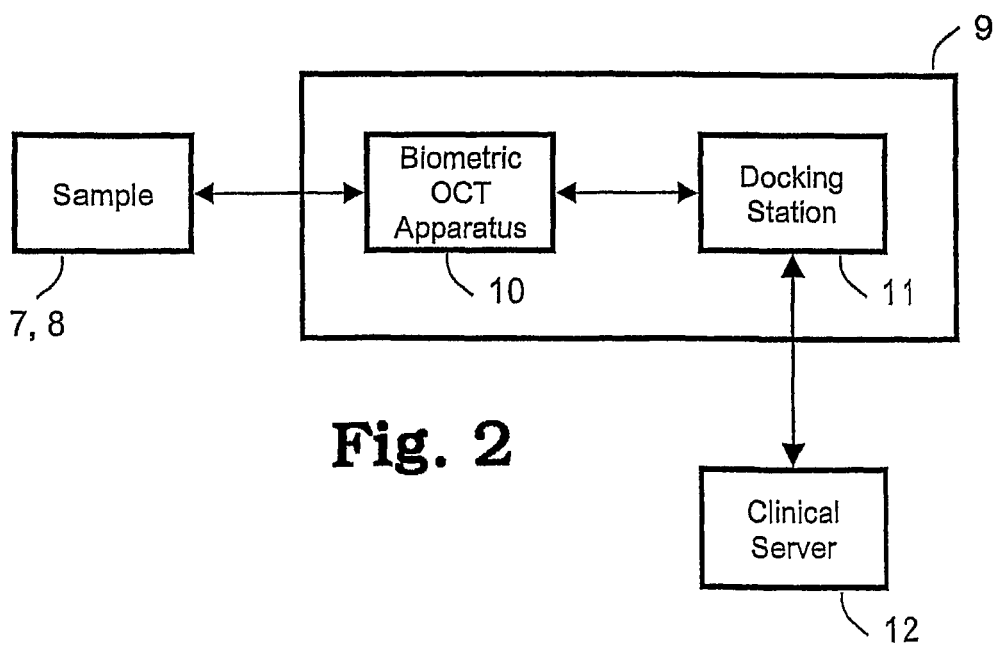
FIG. 2 Block diagram of general architecture of an apparatus according to the invention (Biometric OCT apparatus)

The overall architecture of a biometric OCT appliance according to the invention is depicted in FIG. 2. The system comprises the OCT appliance 9, a clinical server 12, and for the sake of completeness, the "sample", i.e. the eyes 7, 8 to be scrutinized. The OCT appliance is composed of the ophthalmic apparatus (OCT apparatus) 10 and a docking station 11. The docking station 11 serves as primary personal patient-data input system, data memory, performs data postprocessing, recharges the accumulators of the OCT apparatus 10 and holds the OCT apparatus between uses. The docking station 11 can even be used as a holder co-device for scanning a patient suffering e.g. tremor. External devices can be connected to the docking station 11, e.g. a screen, keyboard and others.

Figure 3:
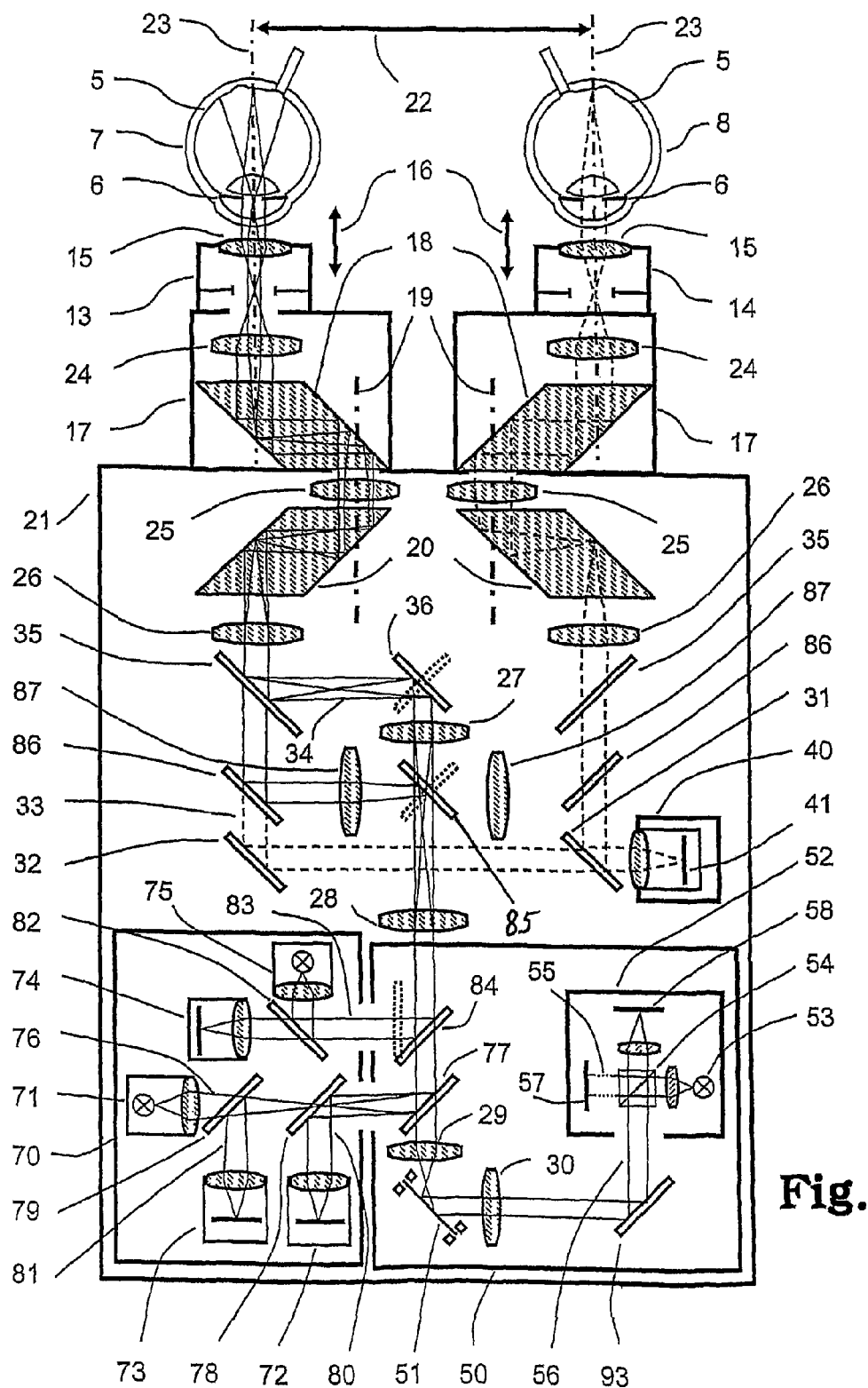
FIG. 3 Detailed diagram of a first embodiment.
Figure 4:
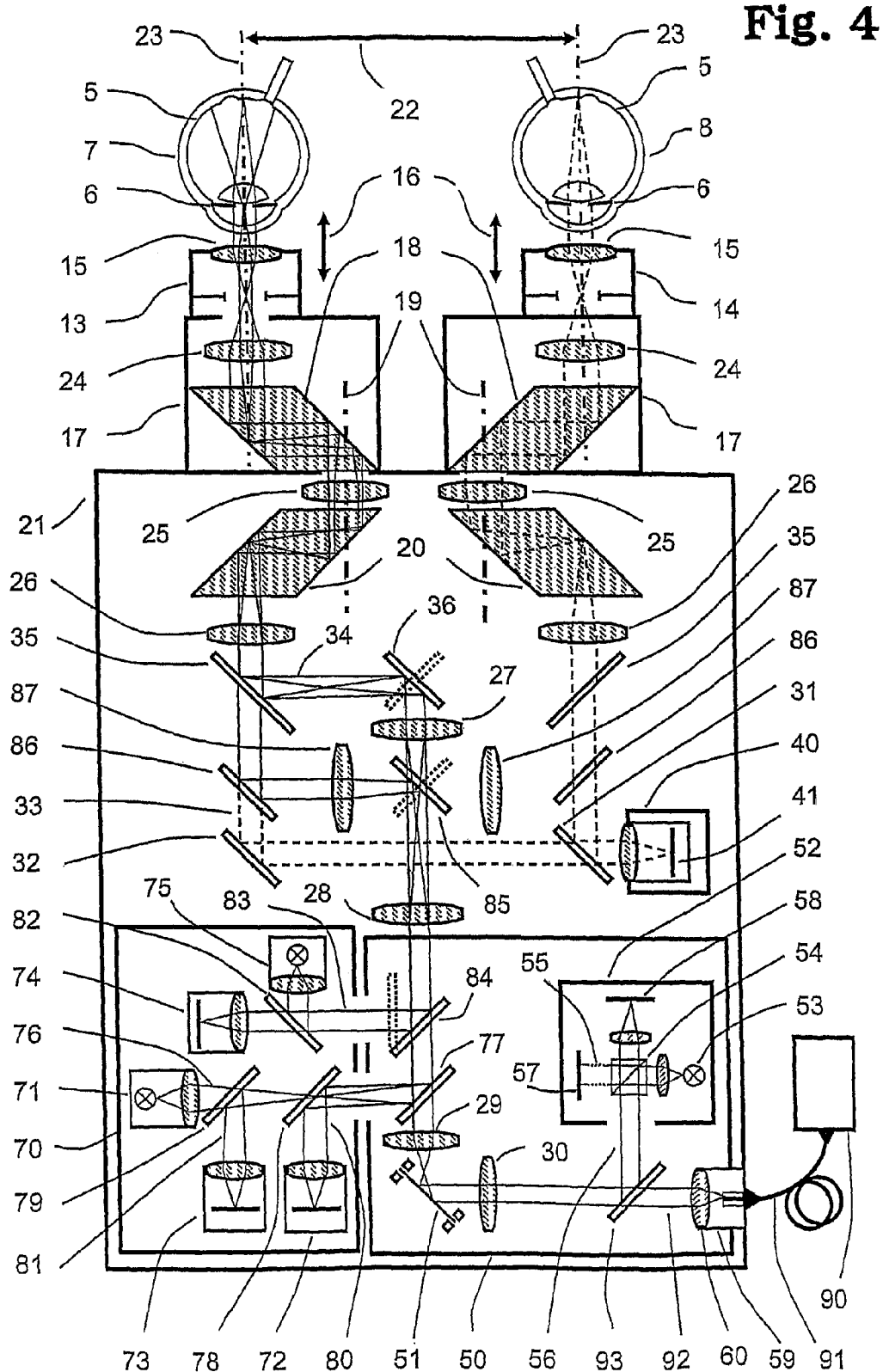
FIG. 4 Detailed diagram of a second embodiment.

The OCT apparatus 10 is preferably cordless. Its details are depicted in FIG. 3 without and in FIG. 4 with Laser therapy provision. Except this difference, the apparatuses of FIGS. 3 and 4 are identical.

The OCT apparatus 10 is binocular, hence capable to scrutinize the right eye 7 and the left eye 8 without the need to move the apparatus and to readjust it to the eye. For each eye 7, 8, it has an ocular module 13, 14 capable to be adjusted to the diopter of respective eye (right ocular module 13 to right eye 7, left ocular module 14 to left eye 8) by moving eye-lenses 15 nearer to or farther away from eyes 7, 8 as indicated by arrow 16. For adapting the distance between the right and left ocular module 13 resp. 14 to the interpupillary distance (IPD), a binocular optics comprises for each eye a movable tube-prism 17 including a prism 18 being rotatable around axis 19 of a fixed prism 20 in the apparatus housing 21. This rotation allows a relative movement (arrow 22) of the oculars 13, 14 to align the optical axis 23 of the ocular 18 to the center of the pupil 6. The optical path from the retina 5 to the fixed prism 20 remains constant. The image conjugate of the retina 5 and the pupil 6 is formed with the help of a series of relay-lenses 24 to 30. Once these adjustments being made, they are locked so that this patient may use the apparatus without repeating them.

Permanently visible by both eyes 7, 8 is the fixation target 41 provided by the fixation target module 40. Light from target (an image displayed at infinity) 41 is partly redirected by semi-transparent mirror 31 to the left eye 8. The part passing mirror 31 is deflected by mirror 32 to the right eye 7.

The ocular-switching mirror 36 is drawn in the position for examining the right eye 7. If turned into the position shown by the dotted line, the left eye 8 is observed.

The visible beam 33 of the fixation target is separated from the near infrared measurement beam 34 by the so-called "hot mirrors" 35. They deflect infrared light used by the measuring parts (fundus camera, OCT device), yet are sufficiently transparent for the light used by the fixation target module 40. Of course, if other light types are used by the mentioned components, the transparency and reflection characteristics of the mirrors 35 may be accordingly modified. Preferably "near infrared" light is used for the measurement components.

The measuring components are the scanner module 50 (OCT module) and the eye-monitoring module 70. The eye monitoring module 70 comprises an auxiliary near infrared light source 71 (wavelength e.g. about 880 nm), the near infrared low resolution fundus camera 72, the four-quadrant NIR detector 73 (4QD) and a high resolution camera 74, operating in the visible range of the optical spectrum, which uses an auxiliary visible illumination module 75.

A large area of the retina 5 of the eye 7 under observation is illuminated by the beam 76 of the auxiliary NIR light source 71. The retro-reflected NIR light from the illuminated retina 5 passes the pupil 6 and travels backwards to the 4QD 73 and the fundus camera 72. From the relay lens 28, the backward NIR light is reflected by a low wavelength pass mirror 77 toward the beam splitters 78 and 79. The image conjugate of the retina is formed by the beam 80 on the fundus camera 72 so that biometric features 3 can be detected in the image 1, while the image conjugate of the eye pupil is formed by the beam 81 on the 4QD 73.

4QD 73 contains 4 detectors each observing the retro-illuminated pupil with the four regions being adjacent or overlapping. The four detectors may each be a point-type optical sensor like an optotransistor. A movement of the eye creates in each sensor a change of received light. Thereby, lateral movements of the examined eye 7 can be detected. The result is used in the evaluation process to determine if the ROI is still observed and in the negative, the observation results are discarded.

Figure 9:
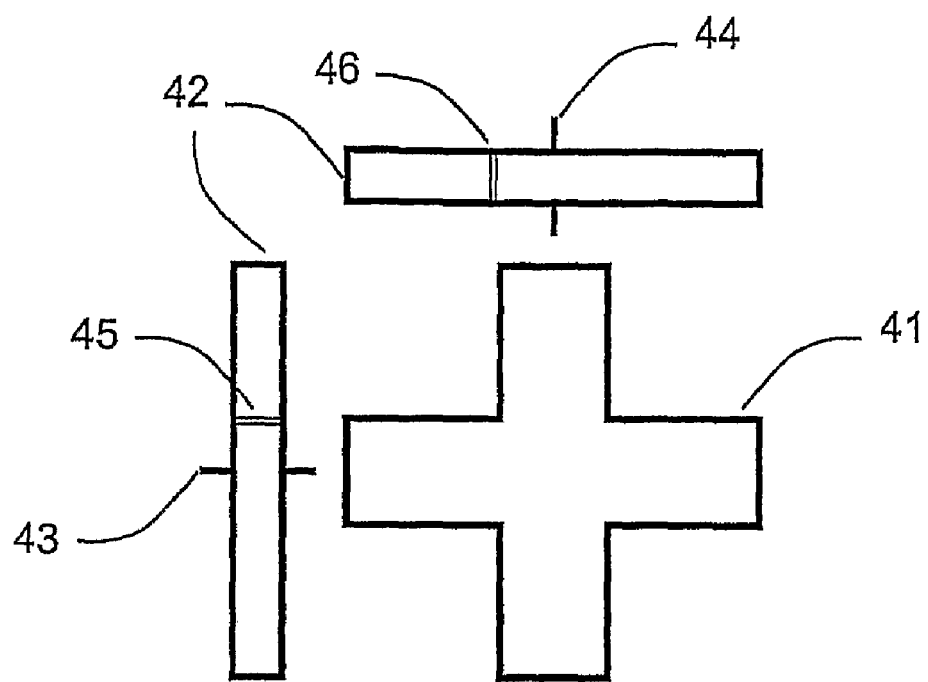
FIG. 9 Fixation target.

For securing the correct relative orientation of the observation direction of the OCT appliance 9 and the examined eye 7 or 8, an alignment method is implemented:

The fixation target module 40 provides an indicator 42 of the present orientation of the eye, e.g. a horizontal and a vertical bar at the borders of the fixation target (cf. FIG. 9). More precisely, this indicator serves to give a feed-back to the patient about the position of the pupil center relative to the optical axis of the OCT apparatus.

Each bar of the indicator 42 has a fixed mark 43,44 for an optimal orientation of the observed eye 7, 8, and an indicator bar 45, 46 for the present vertical resp. horizontal orientation of the eye. The required orientation of the observed eye aligned with the optics of the OCT appliance 10 is attained if the indicators 45, 46 are aligned with fixed marks 43 resp. 44. Of course, many other arrangements and layouts of the fixation target and the orientation indicator 42 are conceivable. E.g., the orientation indicator may be integrated in the fixation target 41. Generally, however, it is preferred to arrange it in a peripheral region so that the patient can observe it even if the central view is disturbed. Another possibility may be to indicate the correct position by a sound or a color, e.g. with red as "too low" and blue as "too high", which of course requires a sufficient capability to discern the used colors. Still to mention that the output of the 4QD may also be used to adjust a head-rest or to position the head of the patient correctly before a stationary apparatus or to hold a hand-held OCT appliance in a correct position and orientation by the patient.

The high resolution fundus camera 74 can detect biometric features 3 in the image 1 with a better resolution in the visible range of the optical spectrum as a complement to the retina diagnostic. After reflection on the beam splitter 82, the visible beam 83 of the auxiliary light source 75 travels toward the eye under observation 7 to illuminate its retina 5. The illumination beam 83 reaches the eye after the following reflections: a reflection on the rotatable mirror 84 for visible light, on the so-called cold rotatable mirror 85 and on the beam splitter 86. The relay lens 87 replaces the relay lens 27 to insure a correct image formation of the intermediate image conjugate of the retina 5. The image conjugate of the retina in the visible light range is formed on the fundus camera 74.

OCT Module

The OCT module 50 (scanner module) of FIG. 3 comprises a scanner 51 and an (OCT) interferometer 52. Generally, an OCT interferometer as known per se may be used, of which a preferred design is described below. OCT interferometer are known to be of the time-domain type with mechanical scanning of the reference beam, or of the frequency-domain type using a Fourier transformation and an optical grating which is either fixed or moveable. With regard to a hand-held appliance, mechanically moved parts are avoided leading to preferring the frequency domain type with fixed grating.

The interferometer 52 contains a white light source 53, i.e. of suited light with a sufficiently broad frequency spectrum (e.g. light with a spectrum width of about 50 nm at about 820 nm wavelength), a beam splitter 54 for splitting the light source's light into a reference beam 55 and a measuring beam 56, a reference beam reflector 57, and an OCT detector 58. Construction and operation of this module, as far as not specifically explained within this description, may be executed according to the state of the art, and a detailed description is not required. By suited optical elements (lenses 29, 30), the measuring beam 56 is focused on the retina of the observed eye, more particularly to the retina within the ROI.

Guided by the image of the fundus camera 72 (cf. below), scanner 51 scans the measurement beam 56 over the ROI 2. The detector 58 together with appropriate evaluation circuitry (not shown) creates an image of the ROI 2 with the OCT-typical information of the region below the surface necessary for discerning any changes in the retina. The OCT detector 58 may be one-dimensional or two-dimensional, and the ROI may be scanned by a light spot or by a light line. The latter needs less time, hence reduces the risk of deterioration by an eye movement, and needs less movable parts, yet requires a more performing evaluation processing arrangement.

Figure 10:
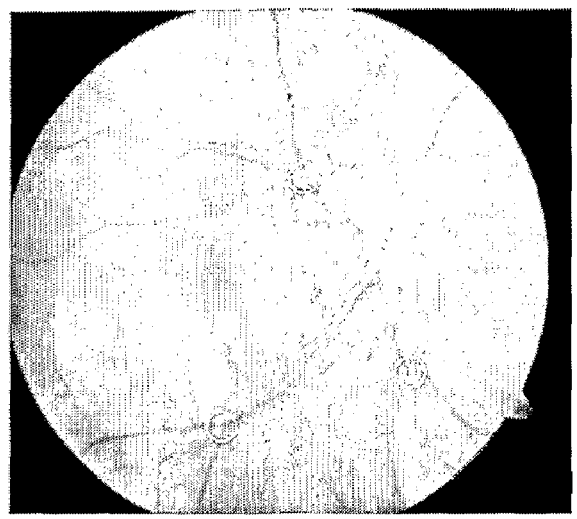
FIG. 10-12 Photographs of the retina with different resolutions.
Figure 11:
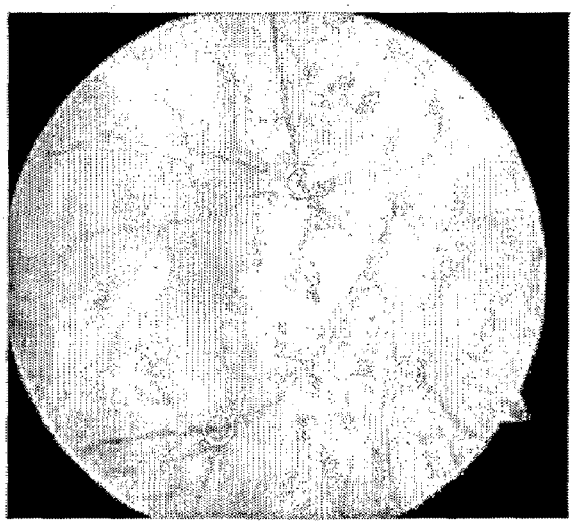
Figure 12:
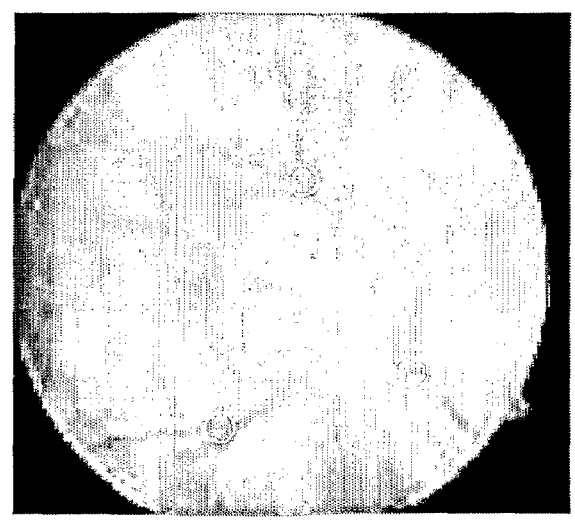

The FIGS. 10-12 show photographs taken by fundus camera 72 using different resolutions:

| Fig. | Pixel size $[10^{-6} m]$ | Line Pairs/mm [lp/mm] | Rel. Resolution |
|---|---|---|---|
| 10 | 2.84 | 44 | 100% |
| 11 | 25.8 | 4.8 | 11% |
| 12 | 47.4 | 2.64 | 6% |

Empirically, a value of about 4 lp/mm is found to be a working compromise between resolution and computational demand. The photographs are taken, as an example, with a visual angle of 36°. The real diameter of the retina image is 10.5 mm.

Surprisingly, even in FIG. 12 with only a low resolution, the biometric features can be clearly detected. Taking into account that the number of pixels used is reduced by the second power, i.e. by about 280, the efforts to localize the biometric features fully automatically by a picture evaluation algorithm is enormously reduced. Generally, the computational effort, e.g. 2D autocorrelation, is proportional to the 4th power of the number of pixels in one dimension. Already for the example of FIG. 11, the calculation time is reduced by a factor $11^4=14641$, i.e. from e.g. 1 h to about ¼ s. This is one important factor for allowing the orientation of the OCT unit directly by means of the low resolution fundus camera.

In practice, it has been determined that the resolution of 4.8 lp/mm, i.e. about 5 lp/mm, allows a perfect alignment with the biometric features with complying with the speed demands of the data processing.

It has further been found that a resolution of 7 pixels per degree of field of view is sufficient for identifying the preferred biometric features, namely vessel bifurcations of the largest vessels which generally show a good contrast. Another biometric feature may be the contour of the optic nerve.

Another preferred reduction of computational demand is a limitation of the region observed. It has been found that a field of 20° comprising the optical disc contains a sufficient number of markers, i.e. biometric features. Thereby, a reduction of the field of view by about 40% of the full field (about 36°) is obtained, and the number of image pixels to be handled is reduced accordingly.

Externally Attachable Accessory

For therapeutic purposes, the OCT module 50 may be provided with a connection 59 for a thermal laser 90. In case of the OCT apparatus 10 to be used by the patient autonomously, the patient will be provided by the OCT apparatus 10 without laser 90 for security reasons. If the ophthalmologist detects a negative development of the patient's retina, he may connect the laser 90 to the OCT apparatus 10 with an appropriate light-guide 91 and may almost immediately start the laser therapy because the OCT appliance, hence also the laser 90, is perfectly adapted to the patient's eyes.

The beam of laser 90 is suitable refracted by lens 60 of connector 59 and inserted in the internal light path of the OCT module by bandpass mirror 93 reflective for the laser's radiation. Hence, the laser beam can be readily directed to the ROI 2 by the scanner 51 of the OCT module 50. As the therapy laser 90 operates in the visible range, the rotatable mirror 84 of the high resolution fundus camera 74 has to be turned so that it allows the laser light to travel toward the relay lens 28. The laser light is reflected on the rotatable high cold mirror 85 (the mirror reflects the visible light of the laser and the fundus camera, yet not the IR light of the OCT module) and on the beam splitter 86. The reflectivity ratio of the beam splitter 86 has to be adequately chosen to provide enough transparency for the target imaging module. The optical power of the target display can be increased accordingly.

Of course, other devices than a laser for therapeutic purposes may as well be connected to the OCT apparatus and profit from its ready-for-use adjusted optical path.

Operation of OCT Appliance

Figure 5:
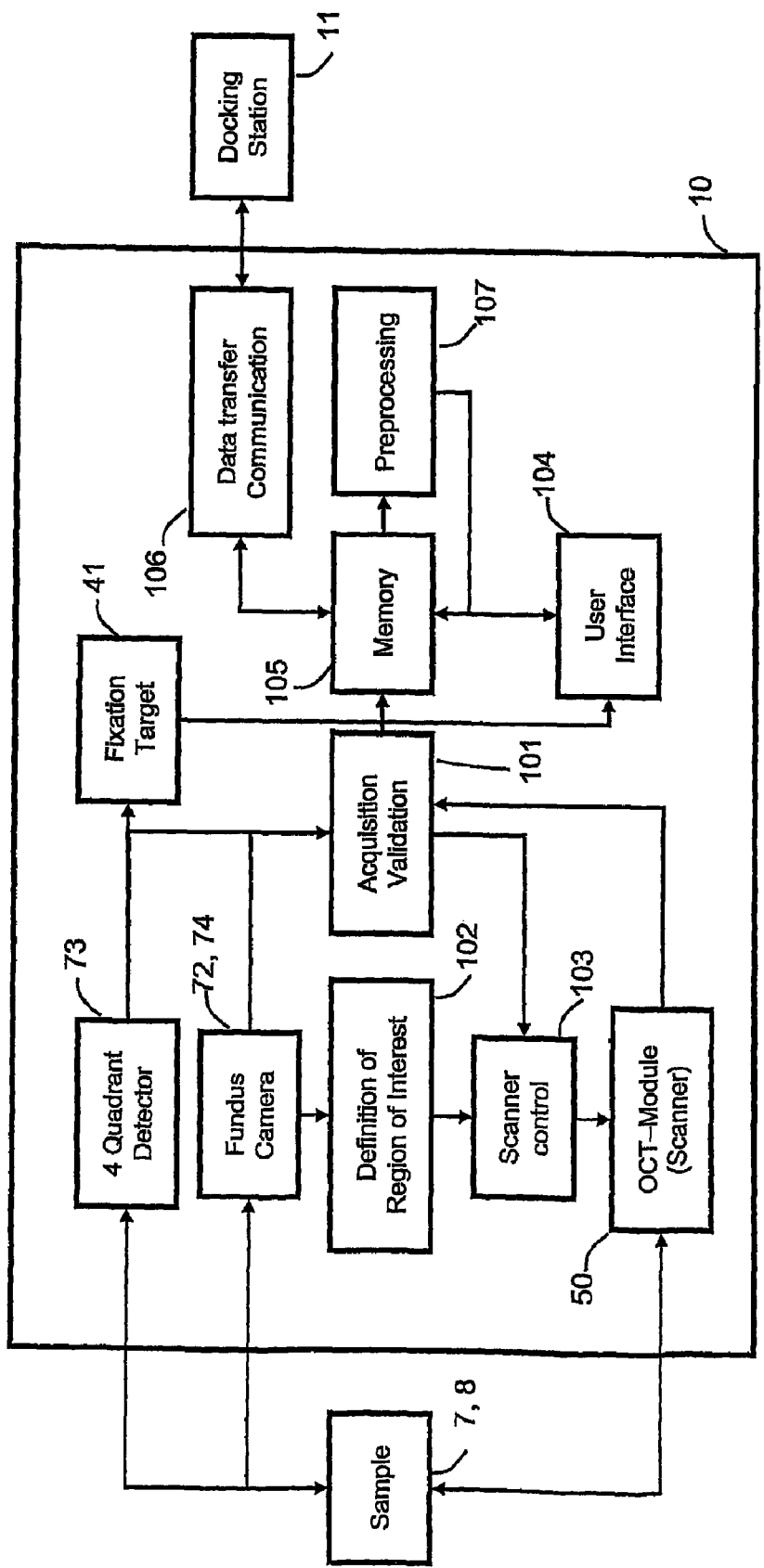
FIG. 5 Flow diagram of OCT eye acquisition.

With reference to FIG. 5, the three measuring modules (fundus camera 72, 4QD 73 and OCT module 50) generate measurement signals and furnish them to the acquisition validation 101. The output of fundus camera 72 is supplied to the definition-of-ROI block 102, too. It identifies the predefined biometric features 3 in the image 1 (FIG. 1) and based thereon the actual position of the ROI 2 relative to the optical axis of the OCT apparatus 10. Using these data, scanner control 103 manages the scanner of the OCT module 50 to scan the ROI 2.

Output of the four-quadrant detector 73 is displayed by the fixation target module 40 which is part of the user interface 104. Data acquisition 101 collects data of the fundus camera 72 and the 4QD 73. If the data indicate that by the most recent scan of the OCT module 50, the ROI 2 has actually been scanned, the scan data are transferred into memory 105, together with, as applicable, data of the fundus camera 72 and the 4QD 73.

The data are subjected to a preprocessing step 107 (data compression; OCT interferogram reduction to specific areas within the ROI etc.). The result is stored again in memory 105 and transferred to the user interface 104. It may be used to show a success/failure indication or other messages (diagnostics, instructions how to continue). Still to mention that user interface 104 may also contain a manual measurement-starting device (trigger). The patient decides to start the measurement in operating the measurement-starting device once the handheld apparatus automatically provides a visual (via the fixation target image) or acoustic signal indicating a correct centering of the device (FIG. 6). The patient will try to keep the apparatus in the correct position during the measurement process. The indicator 42 will help the patient to perform this alignment.

The measurement data remain stored in the memory 105 until the OCT apparatus 10 is put into its docking station 11. The data may relate to one single measurement (one record), may comprise a number of records relating to one patient, or even relate to a number of patients, e.g. in a series checkup. Then, the data are transferred by data transfer and communication block 106 into the docking station 11. Reversely, block 106 is able to take data from the docking station 11 for modifying further measurement. F.i., the ophthalmologist may decide to redefine the ROI 2 after having studied the results.

FIGS. 6 and 7 show more in detail the eye alignment processes before resp. during an OCT measurement. With reference to FIG. 6, the patient observes the eye orientation, or more precisely the deviation of the center of the pupil from the optical axis of the instrument, and waits, until a stable "eye aligned" condition is established. For this purpose, he regards the fixation target 41. The OCT-patient alignment block 130 observes the eye to be measured and displays a feed-back, e.g. the eye orientation indicator 42 within the fixation target 41. Additionally, if present, an automatic OCT-eye misalignment compensation module may support the patient in posing the apparatus 10 and his head correctly. An indication may be furnished that the automatic is within the center of its working area to safeguard a correct ulterior measurement.

Based on the feed-back signals (e.g. visual, acoustical), the patient detects a condition of acceptable alignment between his eye and the OCT appliance ("Acqu. Start—Patient Decision" 131) and triggers the data acquisition 132. It is, however, even conceivable to detect the ready-for-measurement and to start the acquisition automatically.

During data acquisition, the patient decision block 131 is shortcut so that the system is simplified as depicted in FIG. 7, and eye alignment is secured or watched by OCT-patient alignment 130 alone. If alignment is lost, the data acquisition validation discards the measurement.

The functions of the docking station 11 are shown in the block diagram of FIG. 8. The data and instructions are exchanged with the OCT apparatus 10 ("Mobile OCT") by the data transfer and communication unit 110. Instructions and data are stored in memory 111. The measurement results are treated by post-processing unit 112, inter alia for reducing the amount of data. A user interface 113 allows inspection of measurement results and entering data. F.i., the ophthalmologist may have a more elaborate docking station 11 allowing to reprogram the OCT apparatus. The patient's home docking station 11, in contrast, does not provide this functionality or only under control of a remote host like the clinical server 12.

Clinical server 12 is connected via the Internet, telephone line or the like. It serves to collect the measurement data of one or more patients and allows the ophthalmologist to remotely monitor his patients. Of course, the measurement results may be stored on a data carrier like a disk and forwarded in this way to the ophthalmologist, medical service, or specialized centers, too.

Based on the description of the exemplary embodiment, many variants of the invention are conceivable without leaving the scope of protection which is defined by the claims. Some of these variants are:

Design as a monocular and/or stationary device, e.g. for use in a praxis of a professional, still providing the advantage of automatic identification of the ROI and compensation of eye movements. Such a device may be provided with a memory storing the adjustments of each patients. The device may be provided with sufficient actuators so that adjustment to an eye of a patient may be done automatically by activating the corresponding set of adjustments.

The low resolution camera for localizing the biometric features and automatically adjusting the OCT unit may take images which have a maximum resolution of about 2.7 lp/mm and more preferably of at most 5 lp/mm. Alternatively, the resolution is chosen in the range 3 to 5 lp/mm.

The resolution of the low resolution camera is at most 10 pixels per degree of field of view.

The field of view of the low resolution fundus camera used for detecting the biometric features is limited to at most about 25°, preferably 20°.

The reduction of the number of pixels or the size of image to be evaluated is attained by using only a part of the image point values (pixels) furnished by the low resolution fundus camera, and/or by a numerical reduction of the resolution of the camera, e.g. by averaging small areas or more sophisticated methods known in the art per se.

The OCT appliance is Provided with accumulators which are charged each time it is placed in the docking station.

A sensor different from the described four-quadrant detector for tracking or monitoring eye movements.

GLOSSARY

4QD four-quadrant detector
AMD age-related macular disease
FOV Field of view
NIR Near infrared OCT optical coherence tomography
ROI region of interest

What is claimed is:

1. An ophthalmologic appliance for imaging a retina of an eye fundus, the appliance comprising:
    an optical coherence tomography arrangement;
    a camera configured to take an image of the fundus of the eye sufficient to determine a location of characteristic features of the fundus; and
    a director positioned and configured to adjust the arrangement so as to aim automatically at least one observation region of the retina based on a spatial relation between the at least one observation region and the location of the characteristic features of the fundus determined from the image, wherein the camera is a low resolution fundus camera having a resolution of at most 5 lp/mm.

2. The appliance of claim 1, further comprising:
    a controller in operable connection with the camera and the director, and the controller being programmed to determine the characteristic features in the image taken by the camera and to control the director to adjust the arrangement to the at least one observation region.

3. The appliance of claim 1, wherein the camera is a low resolution fundus camera having a resolution of at most 2.7 lp/mm on the retina.

4. The appliance of claim 1, wherein the camera is a low resolution fundus camera with a resolution in a range of 3 to 5 lp/mm.

5. The appliance of claim 1, wherein the camera has a resolution of at most 7 pixels per degree of field of view.

6. The appliance of claim 1, wherein the camera has a field of view of at most 25°.

7. The appliance of claim 1, wherein the appliance is binocular and configured to secure a reproducible position before eyes of a patient.

8. The appliance of claim 7, wherein the appliance includes two ocular modules configured to examine one eye or the other eye of a person without repositioning the apparatus.

9. The appliance of claim 7, wherein the appliance is configured to be adjustable for a person by adjusting at least the interpupillary distance and view properties of the person's eyes, and the appliance comprising a locking unit positioned and configured to lock an adjusted position or to store or to restore the adjusted position.

10. The appliance of claim 1, wherein the camera, the director and the OCT arrangement are together provided as a hand-held device.

11. The appliance of claim 1, wherein the appliance comprises an eye fixation targeter, a pupil position detector and an eye off axis position indicator, the pupil position detector being in operative connection with the eye off axis position indicator, so that the eye off axis position indicator is configured to display a deviation of the eye from a nominal center position.

12. The appliance of claim 1, further comprising an accessory connection configured to couple an external device to the apparatus and to enable a connection for diagnostic or therapeutic interaction with the eye.

13. A system for surveying eye characteristics of a person or an animal comprising an appliance according to claim 1, wherein the appliance comprises a communication unit, and the system further comprises:
    a remote server configured to be connected to the communication unit over a network for data transmission, and configured to receive measurement data transferred from the appliance over the network.

14. The system of claim 13, wherein the server is configured to transfer data to the appliance, and the appliance is configured to be adjusted from a first operating state to a second operating state upon receipt of the transferred data.

15. A method for surveying characteristics of eyes of a person using a system of claim 13, the method comprising collecting data ascertained by the ophtalmic appliance in the server.

16. The appliance of claim 1, wherein the camera has a resolution of at most 10 pixels per degree of field of view.

17. The appliance of claim 1, wherein the camera has a field of view of at most 20°.

18. An ophthalmologic appliance for imaging a retina of an eye fundus, the appliance comprising:
    an optical coherence tomography arrangement;
    a camera configured to take an image of the fundus of the eye sufficient to determine a location of characteristic features of the fundus; and
    a director positioned and configured to adjust the arrangement so as to aim automatically at least one observation region of the retina based on a spatial relation between the at least one observation region and the location of the characteristic features of the fundus determined from the image, wherein the camera has a resolution of at most 7 pixels per degree of field of view.

19. The appliance of claim 18, further comprising:
    a controller in operable connection with the camera and the director, and the controller being programmed to determine the characteristic features in the image taken by the camera and to control the director to adjust the arrangement to the at least one observation region.

20. The appliance of claim 18, wherein the camera has a field of view of at most 25°.

21. The appliance of claim 18, wherein the appliance is binocular and configured to secure a reproducible position before eyes of a patient.

22. The appliance of claim 18, wherein the appliance includes two ocular modules configured to examine one eye or the other eye of a person without repositioning the apparatus.

23. The appliance of claim 18, wherein the camera, the director and the OCT arrangement are together provided as a hand-held device.

24. The appliance of claim 18, wherein the appliance comprises an eye fixation targeter, a pupil position detector and an eye off axis position indicator, the pupil position detector being in operative connection with the eye off axis position indicator, so that the eye off axis position indicator is configured to display a deviation of the eye from a nominal center position.

25. The appliance of claim 18, further comprising an accessory connection configured to couple an external device to the apparatus and to enable a connection for diagnostic or therapeutic interaction with the eye.

26. An ophthalmologic appliance for imaging a retina of an eye fundus, the appliance comprising:
    an optical coherence tomography arrangement;
    a camera configured to take an image of the fundus of the eye sufficient to determine a location of characteristic features of the fundus; and
    a director positioned and configured to adjust the arrangement so as to aim automatically at least one observation region of the retina based on a spatial relation between the at least one observation region and the location of the characteristic features of the fundus determined from the image, wherein the appliance is binocular and configured to secure a reproducible position before eyes of a patient, and wherein the appliance is configured to be adjustable for a person by adjusting at least the interpupillary distance and view properties of the person's eyes, and the appliance comprising a locking unit positioned and configured to lock an adjusted position or to store or to restore the adjusted position.

27. A system for surveying eye characteristics of a person or an animal comprising an appliance according to claim 26, wherein the appliance comprises a communication unit, and the system further comprises:
a remote server configured to be connected to the communication unit over a network for data transmission, and configured to receive measurement data transferred from the appliance over the network.

28. The system of claim 27, wherein the server is configured to transfer data to the appliance, and the appliance is configured to be adjusted from a first operating state to a second operating state upon receipt of the transferred data.

29. A method for surveying characteristics of eyes of a person using a system of claim 27, the method comprising collecting data ascertained by the ophtalmic appliance in the server.

* * * * *